(12) United States Patent
Ericsson et al.

(10) Patent No.: US 6,255,385 B1
(45) Date of Patent: Jul. 3, 2001

(54) POLYHYDROXY POLYMERS SUBSTITUTED WITH STYRYL ETHER GROUPS AND GELS AND SURFACES PREPARED FROM THEM

(76) Inventors: Jan Ericsson, Drottninggatan 121, S-254 33 Helsingborg; Charlotta Lindquist, Gropgränd 4, S-753 10 Uppsala, both of (SE)

( * ) Notice: Subject to any disclaimer, the term of this patent is extended or adjusted under 35 U.S.C. 154(b) by 0 days.

(21) Appl. No.: 09/117,679
(22) PCT Filed: Jul. 15, 1998
(86) PCT No.: PCT/SE97/00255
    § 371 Date: May 11, 1999
    § 102(e) Date: May 11, 1999
(87) PCT Pub. No.: WO97/31026
    PCT Pub. Date: Aug. 28, 1997

(30) Foreign Application Priority Data

Feb. 20, 1996 (SE) .................................................. 9600612

(51) Int. Cl.$^7$ .............................. C08H 1/00; C08B 37/02; C08J 7/04
(52) U.S. Cl. ........................... 525/42; 525/56; 526/238.2; 526/288.21; 526/332; 526/333; 526/334; 527/300; 527/315
(58) Field of Search .................... 525/42, 56; 576/238.2, 576/238.21, 332, 333, 334; 527/300, 315

(56) References Cited

U.S. PATENT DOCUMENTS 3,882,084 * 5/1975 Tato et al. ............................. 526/245

* cited by examiner

Primary Examiner—Nathan M. Nutter
(74) Attorney, Agent, or Firm—Royal N. Ronning, Jr.

(57) ABSTRACT

A polyhydroxy polymer substituted with covalently linked alkene groups, characterized in that the alkene groups are styryl ether groups. A gel obtained by polymerization of a styryl ether substituted polyhydroxy polymer. A surface that has been hydrophilized by adsorption of a styryl ether polyhydroxy polymer.

7 Claims, No Drawings

POLYHYDROXY POLYMERS SUBSTITUTED WITH STYRYL ETHER GROUPS AND GELS AND SURFACES PREPARED FROM THEM

This application claims priority to PCT Application Number PCT/SE97/00255, filed Feb. 17, 1997, which, in turn, claims priority to Swedish Patent Application 96 00612-7 filed Feb. 20, 1996.

1. Technical Field

The present invention concerns novel polyhydroxy polymers substituted with alkene group-containing substituents and polymerised forms of such polymers. These polymers comply with the general formula

R—B—P, where R is an alkene group, B is an organic bridge and P is a polyhydroxy polymer and contains additional groups R—B—. P without any groups R—B— is designated P'. In the invention the alkene group is a styryl ether group. The inventive polymer will further on be called styryl ether polyhydroxy polymers.

R—B—P polymers have earlier been used for the manufacture of separation media for biorganic molecules and as hydrophilization agents etc. Potential fields of use encompass a) supports for the synthesis of oligopeptides and oligonucleotides, b) carriers for cell culture, c) carriers for enzymes, e) amphiphilic polymers etc and novel starting material for these types of supports, carriers, media, polymers etc.

2. Technical Background

The polyhydroxy polymers (P') used so far for the synthesis of separation media have been based on native polymers, such as dextran, agarose, cellulose, starch etc, or synthetic polymers, such as poly(hydroxy alkyl acrylates) including corresponding poly(methacrylates). These separation media have been used in gel forms, i.e. swelled in the liquid in which they are to be used. In order to achieve the proper rigidity, porosity etc, the degree of cross-linking etc, the type of cross-linker, concentrations of cross-linker and polymer etc have been varied. The liquids used in the context of biotechnological applications have been water and mixtures of water and water miscible liquids, such as methanol, ethanol, isopropanol, acrylonitrile and water-miscible mixtures of liquids.

Polymers R—B—P have earlier been suggested as base constituents for the manufacture of separation media (Söderberg L., U.S. Pat. No. 4,094,832 (dextran) and U.S. Pat. No. 4,094,833 (dextran), and Nochumsson S, EP 87,995 (agarose)). The suggested uses have been as media for electrophoresis, liquid chromatography, such as gel permeation chromatography and various forms of affinity chromatography (ion exchange, hydrophobic, covalent, biospecific affinity etc chromatography).

It has also been suggested to adsorb polyhydroxy polymers substituted with hydrophobic groups onto surfaces in order to hydrophilise hydrophobic surfaces and obtain surface-bound gel layers (Henis et al., U.S. Pat. Nos. 4,794, 002 and 5,139,881; and Varady L et al., U.S. Pat. No. 5,030,352). The adsorbed layers have often been stabilised by crosslinking. For hydrophobic groups containing an alkene structure, grafting has been suggested (Allmér K., WO 9529203).

In earlier publications the alkene group (R) has been allyl, such as in allyl glycidyl, and acryl/methacryl. See Allmér K., WO 9529203; Söderberg L., U.S. Pat. Nos. 4,094,832 and 4,094,833; and Nochumsson S, EP 87,995.

The bridge B has been stable against hydrolysis in the pH-range 2–14 and inert in the separation process contemplated.

Drawbacks of Earlier used Polyhydroxy Polymers

There have been certain drawbacks with the prior art separation media. Those based on native polymers have often exhibited a poor rigidity. This has implicated the manufacture of media based on synthetic polymers, such as styrene-divinyl benzene copolymers and the like, which in many cases have had an improved mechanical and chemical stability. However, the resulting polymers often have had a hydrophobic character promoting non-desired protein adsorption.

With respect to hydrophilisation, the prior art polymers often give poor adsorption steps. The stabilisation step (grafting/cross-linking) has often meant a reduction of the adsorbed layer.

Objectives of the Present Invention

The main objectives of the present invention is to provide alternative separation media and other supports/carriers that are favourable with respect to hydrophilic/hydrophobic balance, chemical and mechanical stability (including rigidity), methods of manufacture etc.

Other objectives are to provide alternative hydrophilisation processes that result in favourable properties as given for the media and supports/carriers.

Still other objectives are to provide alternative a) supports for the synthesis of oligopeptides and oligonucleotides, b) carriers for cell culture, c) carriers for enzymes, e) amphiphilic polymers etc and novel starting material for these types of supports, carriers, media, polymers etc.

The Invention

We have now found that styryl ether polyhydroxy polymers can be used for the manufacture of separation media and carriers/supports as described above. The higher reactivity of the styryl ether group compared to e.g. an allyl group gives an advantageous situation as far as the polymerisation is concerned. The main aspect of the present invention thus is an alkene group-containing polyhydroxy polymer as defined in the introductory part, the characteristic feature being that the alkene group (R) is a styryl ether group ($CH_2$=$CHC_6H_4O$—), where the —O— grouping preferably is orto or para to the alkene group, without exclusion of the meta position. The aromatic ring may be substituted by, for example, one or more lower alkyl groups ($C_{1-6}$), one or more lower alkoxy groups ($C_{1-6}$), one or more halogens (such as chlorine) etc. The alkene group may be substituted with a lower alkyl ($C_{1-3}$) and/or a lower alkoxy group ($C_{1-3}$) or any other group not destroying the reactivity of the alkene group. If not otherwise specified, the expression "styryl ether group" includes substituted forms.

Other aspects of the invention are polymerised forms of styryl ether polyhydroxy polymers and their use as described under the headings Technical Field and Technical Background.

The polyhydroxy polymer (P') may be a biopolymer, preferably with carbohydrate structure, such as in dextran, cellulose, agarose, starch and other water-soluble or water-insoluble polysaccharides. P' may also be selected among synthetic polymers, such as polyvinyl alcohols, polymers based on vinyl hydroxyalkyl ethers, polymers based on hydroxyalkyl acrylates or methacrylates. Preferred polymers are water-soluble. Polymers that inherently are water-insoluble can be derivatised to become water-soluble. Among the specific polymers mentioned the preference is for dextran. P' exhibit may groups other than R—B— as known in the field of chromatography. See below.

The bridge B is selected according to the rules mentioned under the heading Technical Background. Typically B contains one or more straight, branched or cyclic hydrocarbon chains that may be substituted with one or more hydroxy groups or broken by one or more ether oxygens. In order to secure a high stability against hydrolysis, it is preferred to have no more than one oxygen atom bound to each carbon atom of the hydrocarbon chain. Compared to ether groups, thioether (—S—) and sulphonamide (—SO$_2$NH—) groups have a comparable or higher hydrolytic stability. They can thus also be present or equivalently replace ether oxygens in the hydrocarbon chain. Similarly, hydroxy groups and hydrogens may be replaced by lower alkoxies (C$_{1-6}$) that in turn may contain ether or hydroxy groups. The structure of the bridge B depends on this coupling techniques employed to provide the polymer with styryl ether groups. The R—B— group is normally attached to the polymer via an ether linkage utilizing a hydroxy oxygen of the polymer.

The styrene derivatised polymer may be synthesised by reacting a polyhydroxy polymer with a styryl alkylene ether derivative CH$_2$=CHC$_6$H$_4$OR'L, where R' is a hydrocarbon chain of the type mentioned for B, and L is a group reacting with nucleophiles, such as hydroxy groups. L may be halo, epoxy etc. Compounds CH$_2$=CHC$_6$H$_4$OR'L may be obtained by reacting:

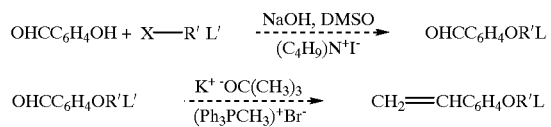

where X is a nucleophile that is displaced by the hydroxy group of OHCC$_6$H$_4$OH (i.e. —O$^-$), R' has the same meaning as previously, and L' may be equal to L (and is then stable under the reaction conditions applied) or a group that can be transformed to L. Examples of the compound X—R'L' are epichlorohydrin and hydroxyalkyl dihalides. The solvent may vary depending on selected reactants, with water and dimethyl sulphoxide (DMSO) as illustrative examples. Alternative reaction routes involve reacting CH$_2$=CHC$_6$H$_4$OH or corresponding phenolate with a compound X—R'L'.

Normally the mean molecular weight of the unsubstituted polymer should be within 1,000–10,000,000, in particular 10,000–1,000,000. The degree of substitution (mol-% per monomeric unit) with respect to styryl groups may vary with the polyhydroxy polymer used. It is normally below one styryl group per monomeric unit of the polymer (100 mol %), such as below 50 mol-% or below 10 mol-%. An illustrative range is 1–30 mol-%. These values are particularly applicable for polysaccharides, e.g. dextran.

The conditions for the polymerisation process are the same as those commonly used for free radical polymerisation of compounds containing styryl or other vinyl groups. The free radical process may be induced by thermally activated initiators, such as peroxides, azo compounds, persulphates etc., and in some cases accelerators, such as amines, may be added. Initiating moieties may also be created by utilizing photoinitiators. Several additional techniques are available in order to create initiating free radicals. This includes electron beam radiation, γ-radiation, redox systems and plasma processes. The preferred conditions may be obtained by optimizing the polymer concentration, the degree of substitution, the temperature, the choice of solvent, the initiating system etc.

Crosslinking/polymerization may also be carried out by conventional crosslinking acting through nucleophilic/electrophilic displacement reactions, for instance by the use of bisepoxides and epihalohydrins.

In analogy with what has been suggested for alkene derivatised dextrans and agaroses (Söderberg L., U.S. Pat. Nos. 4,094,832 and 4,094,832 and Nochumsson S, EP 87,995), styryl ether polyhydroxy polymers may be copolymerised with other vinyl compounds (normally a monovinyl or a divinyl compound), such as styrene, divinyl benzene, acryl or methacryl amides that may be substituted at a nitrogen atom or at a double bound carbon atom, and other vinyl compounds. Typically the amount of styryl derivatised polymer, in particular styryl ether derivatised dextran, constitutes 20–100% (w/w) of the total amount of polymerisable reactants.

Hydrophilic layers, for instance in the form of gels, may be produced on hydrophobic surfaces, for instance by adsorption followed by crosslinking and/or grafting. Se for instance the techniques presented by Henis et al., U.S. Pat. Nos. 4,794,002 and 5,139,881; and Varady L et al., U.S. Pat. No. 5,030,352; and Allmér K., WO 9529203). Suitable substrates to be coated are inner-walls of tubes, porous matrices in the forms of beads, pads, monoliths etc. Typical materials for the substrates are polyacrylates, polymethacrylates, styryl-divinyl benzene copolymers etc.

The ready made gel/surface may contain additional groups providing specific separation characteristics, for instance affinity groups, such as ion exchange groups, hydrophobic groups, antigens/haptens, antibodies, groups allowing covalent chromatography etc. These groups may be introduced either before or after the polymerisation reaction.

The novel styryl derivatised polymers and gels will found uses in the field indicated in heading Technical Field and Technical Background.

EXPERIMENTAL PART

EXAMPLE 1

Synthesis of Styryl Glycidyl Ether

A. Synthesis of 4-(2,3-Epoxypropoxy)benzaldehyde:

4-hydroxy-benzaldehyde (60 g, 491 mmole), NaOH (24 mg, 60 mmole) tetra-n-butyl ammonium iodide (1.5 g) and dimethyl sulphoxide (DMSO, 50 ml) were mixed in a round-bottomed reaction vessel. Epichlorohydrin (112 mg, 1200 mmole) was added drop-wise during 30 minutes and the temperature was raised to 70° C. After 6 hrs at this temperature and cooling, the reaction mixture was poured into 800 ml of water. The organic phase was collected and the aqueous phase was washed with diethyl ether (3×200 ml). The combined organic phase was washed with saturated NaCl (aq) and dried with magnesium sulphate. After evaporation of diethyl ether the product was distilled at 0.29 mbar and 110–111° C. The product was obtained as a clear liquid (25 g) and its $^1$H and $^{13}$C NMR spectra were in agreement with the desired product. Yield: 29%.

B. Synthesis of Styryl Glycidyl Ether

Methyl-triphenyl phosphonium bromide (53.6 g, 150 mmole) was suspended in dry tetrahydrofuran (THF, 250 ml). Then a catalytic amount of 18-crown-6 ether (1 g) was added followed by addition of potassium t-butoxide (17,7 g, 157 mmole) at 0° C. under argon atmosphere. The colour changed from white to yellow and the mixture was stirred for 45 minutes. Thereafter 4-(2,3-epoxypropoxy) benzaldehyde (25 g, 140 mmole) dissolved in dry THF (100 ml) at 0° C. was added and allowed to react for 3 hours. KBr was removed by centrifugation and after decantation the liquid phase was evaporated to a residual oil. The oil was dissolved in diethyl ether and phosphine oxide was allowed to precipitate in the refrigerator over night. After filtration through silica gel followed by evaporation and drying for one hour in vacuum at room temperature, a light-yellow liquid (17.2 g) was obtained and identified by $^1$H NMR to be styryl glycidyl ether. Yield: 70%.

EXAMPLE 2

Synthesis of Styryl Dextran. Dextrans with Mw 40,000 and 500,000

A. Synthesis with NaOH as base (only Dextran with Mw 40,000):

The amounts (dextran and styryl glycidyl ether), solvents and results are presented in table 1 (Exp. 1–8).

Dextran was dissolved in the solvent whereafter a catalytic amount of sodium borohydride, NaOH (45%, aq) and tetra-n-butyl ammonium iodide (0.1 g, only experiments 1–4 and 6–7) were added. Thereafter, styryl glycidyl ether was added with stirring, and the reaction mixture was warmed to 60° C. The reaction was then allowed to proceed over night (about 18 hours). Finally the solution was neutralised with acetic acid at pH 6, and the product styryl dextran was purified by precipitation in ethanol (3×).

B. Synthesis with Dimsyl Sodium ($CH_3SOCH_2^-Na^+$) as the base (Dextrans with Mw 40,000 and 500,000):

The amounts (dextran and styryl glycidyl ether), solvents and results for dextran with Mw 40,000 are presented in table 1, (Exp. 9–11). For dextran with Mw 500,000 the corresponding information is given in table 2.

Sodium hydride (80% in oil, 3.13 g) was suspended in petroleum ether (25 ml) in a sealed flask under nitrogen atmosphere. The hydride was allowed to settle, whereafter the liquid was decanted. This procedure was repeated twice. The sodium hydride was then dried by the use of nitrogen, and DMSO (65 ml) was added to the vessel which was sealed with a septum. Nitrogen gas was bubbled through the liquid via two injection cannulas. The vessel was then placed in an ultra-sound bath and warmed to 60° C. Hydrogen gas was released and vented through an injection cannula. After about 4 hours, when no more hydrogen gas was released, dimsyl sodium was ready to be used.

Dextran was then dissolved in DMSO in a sealed flask with a stirring magnet and the bottle was dried by the use of nitrogen gas and two injection cannulas. Thereafter dimsyl sodium (2 M) was dropped from an injection syringe into the bottle. The vessel was then placed in an ultra-sound bath at 25° C. for 30 minutes and allowed to stand at room temperature for the night. The vessel was then warmed to 60° C. and styryl glycidyl ether added drop-wise with stirring. The reaction was allowed to proceed for 4 hours at the same temperature, whereafter the vessel was placed in an ultra-sound bath at room temperature for 1 hour. The styryl dextran was worked up by precipitation in ethanol (3×).

The content of styryl groups for each of the experiments was determined by NMR. Reactions in aqueous solutions with NaOH as base gave a relatively low degree of substitution, not more than 5% (exp. 1–8). By changing to an aprotic solvent and a stronger base such as dimsyl sodium the degree of substitution could be raised (exp. 9–11).

EXAMPLE 3

Polymerisation

A. Polymerisation of Dissolved Styryl Dextran (Mw 40,000):

The conditions (amounts, degree of substitution, solvent, initiator etc) and results are given in table 3A.

In a typical procedure styryl dextran and initiator were dissolved in the solvent whereafter argon gas was bubbled through the solution. The mixture was then polymerised at 50° C. over night.

No gel was formed when styryl ether dextran (substitution degree 5-mol-%) was polymerised in water. For higher degrees of substitution (30 mol-% and upwards), solvents such as DMSO or triethylene glycol were required for obtaining solutions. Gel formation was observed when polymerising solutions of the higher substituted dextran.

B. Polymerisation of Dissolved Styryl Dextran (Mw 500,000):

In a representative example styryl dextran (0.13 g) was dissolved in water (2 ml) containing the initiator (1.0 mg, ammonium persulphate (APS)). To this, N,N,N',N'-tetramethylene diamine (TEMED) (1 µl) was added as an accelerator for the polymerisation. The gel was formed at room temperature. All the gels prepared were water-swellable. The results and conditions are given in table 3B.

EXAMPLE 4

Electrophoresis on a Gel prepared from Styryl Dextran

Styryl ether dextran with a degree of substitution of 2.8% was dissolved in a urea (7 M) containing tris-HCl buffer (0.375 M, pH 8.8) to a concentration of 15% (w/v). The styryl ether dextran was polymerized to a gel with a radical initiator. Electrophoresis of A sample containing double-stranded DNA was then subjected to electrophoresis in the gel. This resulted in bands which illustrated that obtained the gel has a potential as a medium for electrophoretic applications.

EXAMPLE 5

Hydrophilisation of a Porous Styrene-divinyl Benzene Copolymer Matrix

A porous styrene-divinyl benzene copolymer matrix was soaked with a a water solution containing styryl ether dextran. After removal of the solvent and washing with water and/or dimethyl sulphoxide, the matrix was analyzed by FTIR (Fourier Transform Infrared Spectroscopy). The analysis showed that the matrix had been hydrophilized.

TABLE 1

Example 1. Optimisation for the synthesis of styryl dextran.

| Exp. | dextran (g) | styryl glycidyl (g) | Solvent (ml) | Substitution | Base[1] (mmole) |
|---|---|---|---|---|---|
| 1 | 1.85 | 1 | $H_2O$ 15 | 5% | 9[2] |
| 2 | 1.85 | 1 | toluen/$H_2O$ 10 + 10 | 4% | 9[2] |
| 3 | 4 | 2.82 | toluen/ 15 + 15 | 1% | 19[2] |
| 4 | 4 | 2.82 | $H_2O$ 30 | 5% | 19[2] |
| 5 | 4 | 2.82 | $H_2O$ 30 | 1% | 19[2,3] |
| 6 | 4 | 2.82 | DMF/$H_2O$ 20 + 10 | 1% | 19[2] |
| 7 | 4 | 2.82 | DMSO/H 20 + 10 | 0% | 19[2] |
| 8 | 4 | 2.82 | DMSO 20 | 5% | 19[2] |
| 9 | 1 | 1.06 | DMSO 20 | 38% | 6[3] |
| 10 | 0.83 | 0.9 | DMSO | 38% | 5[3] |

TABLE 1-continued

Example 1. Optimisation for the synthesis of styryl dextran.

| Exp. | dextran (g) | styryl glycidyl (g) | Solvent (ml) | Substitution | Base[1] (mmole) |
|---|---|---|---|---|---|
| 11 | 5 | 5.46 | 15 DMSO 60 | 30% | 30[3] |

[1] A phase transfer catalyst (0.1 g tetrabutyl ammonium iodide) was used in experiments 1–4 and 6–7.
[2] The base was NaOH.
[3] The base was sodium dimsyl.

TABLE 2

Example 2. Syntheses of styryl dextran (Mw 500 000).

| Exp. | Dextran (g) | DMSO (ml) | styryl glycidyl ether (g) | Deg. Subst. (%) |
|---|---|---|---|---|
| 1 | 0.91 | 15 | 0.5 | 1.3 |
| 2 | 10 | 180 | 1.37 | 2.6 |
| 3 | 10 | 300 | 2.71 | 3.6 |

TABLE 3A

Example 3A. Variations in polymerizations with styryl dextran (Mw 40,000).

| Exp. | Subst. Degr. styryl dextran | weight-% polymer | Solvent | Initiator | Gel |
|---|---|---|---|---|---|
| 1 | 5% | 1.8 | $H_2O$ | $K_2S_2O_8$ | no |
| 2 | 30% | 6.5 | $DMSO/H_2O$ | $K_2S_2O_8$ | yes |
| 3 | 30% | 2 | $DMSO/H_2O$ | V-65[1] | no |
| 4 | 30% | 6.5 | $DMSO/H_2O$ | V-65[1] | yes |
| 5 | 30% | 2 | $DMSO/H_2O$ | $K_2S_2O_8$ | yes |
| 6 | 30% | 6.5 | $H_2O$ | $K_2S_2O_8$ | no |
| 7 | 30% | 6.5 | DMSO | $K_2S_2O_8$ | yes |
| 8 | 30% | 6.5 | DMSO | V-65[1] | yes |
| 9 | 30% | 6.5 | $DMSO/H_2O$ | $K_2S_2O_8$ | no |
| 10 | 30% | 2 | DMSO | V-65[1] | no |
| 11 | 30% | 2 | DMSO | $K_2S_2O_8$ | yes |
| 12 | 50% | 6.5 | triethylene glycol | $K_2S_2O_8$ | yes |
| 13 | 50% | 2 | triethylene glycol | $K_2S_2O_8$ | yes |

[1] 2,2'-azobis-2,4-dimethyl valeronitril (Polyscience Inc. U.S.A.)

TABLE 3B

Example 3B. Polymerisation of styryl dextran (Mw 500 000)

| Exp. | Degr. Subst. styryl dextran % | Content % | Initiator | Accelerator | Gel |
|---|---|---|---|---|---|
| 1 | 1.3% | 6.5 | APS | TEMED | yes |
| 2 | 2.6% | 6.5 | APS | TEMED | yes |
| 3 | 3% | 6.5 | APS | TEMED | yes |

APS = ammonium persulphate.
TEMED = N,N,N',N'-tetramethylene diammine.

What is claimed is:

1. A polyhydroxy polymer substituted with covalently linked alkene groups, characterized in that the alkene groups are styryl ether groups.

2. The polyhydroxy polymer according to claim 1, characterized in that the polymer is a polysaccharide.

3. The polyhydroxy polymer according to anyone of claim 1, characterized in that the polymer is dextran.

4. The polyhydroxy polymer according to anyone of claim 1, characterized in that it complies with the general formula

R—B—P, where R is $CH_2$=$CHC_6H_4O$—, B is an inert and stable organic bridge, and P contains additional groups R—B—.

5. The polyhydroxy polymer according to anyone of claim 1, characterized in that B is a straight, branched or cyclic hydrocarbon chain that may be broken by one or more ether oxygens or substituted with one or more hydroxy group or lower alkoxy groups, provided that no more than one oxygen atom binds to one and the same carbon atom.

6. The polyhydroxy polymer according to anyone of claim 1, characterized in that B links to the polyhydroxy polymer via an ether oxygen derived from the unsubstituted polyhydroxy polymer.

7. A Gel obtained by polymerisation of the styryl derivatized polymers defined in anyone of claim 1.

* * * * *